(12) United States Patent
Hahm et al.

(10) Patent No.: US 7,776,873 B2
(45) Date of Patent: Aug. 17, 2010

(54) METHOD FOR TREATING DAMAGE TO GASTRIC MUCOSA

(75) Inventors: Ki-Baik Hahm, Seongnam-si (KR);
Dong-Kyu Kim, Suwon-si (KR);
Mi-Sun Kwak, Gunpo-si (KR);
Sang-Aun Joo, Seoul (KR);
Byoung-Seok Moon, Uiwang-si (KR);
Geun-Seog Song, Anyang-si (KR)

(73) Assignee: Yuhan Corporation, Seoul (KR)

( * ) Notice: Subject to any disclaimer, the term of this patent is extended or adjusted under 35 U.S.C. 154(b) by 134 days.

(21) Appl. No.: 11/604,269

(22) Filed: Nov. 27, 2006

(65) Prior Publication Data

US 2007/0129391 A1    Jun. 7, 2007

(30) Foreign Application Priority Data

Dec. 1, 2005    (KR) .................... 10-2005-0116567

(51) Int. Cl.
*A61K 31/506* (2006.01)
(52) U.S. Cl. ...................................... 514/275
(58) Field of Classification Search ........................ None
See application file for complete search history.

(56) References Cited

U.S. PATENT DOCUMENTS

2005/0249811 A1 * 11/2005 Plachetka .................. 424/472

FOREIGN PATENT DOCUMENTS

| WO | WO 96/05177 A1 | 2/1996 |
| WO | WO 97/42186 A1 | 11/1997 |
| WO | WO 98/18784 A1 | 5/1998 |

OTHER PUBLICATIONS

Antiulcer drug—revaprazan, http://www.manufacturingchemist.com/story.asp?storyCode=30005&sectioncode=81, Dec. 1, 2004.*
Sorbera et al., Drugs of the Future (2004), 29(5), 455-459.*
Johansson, C., Scandinavian Journal of Gastroenterology, 22(S128) (1987), pp. 24-31 (Abstract).*
Tarnawski, et al., Scandinavian Journal of Gastroenterology, 25(174), (1990), pp. 9-14 (Abstract).*
Konturek, P.C., Journal of Physiology and Pharmacology, (1997), 48(1), pp. 9-42 (Abstract).*
"Peptic Ulcer Disease," Curr. Probl. Surgery, vol. 42: 346-454, Jun. 2005.
G. Glavin, et al.: "Experimental gastric mucousal injury: laboratory models reveal mechanisms of pathogenesis and new therapeutic strategies," The FASEB Journal, vol. 6, pp. 825-831, Feb. 1992.
K. Jain, et al.: "Recent advances in proton pump inhibitors and management of acid-peptic disorders," Bioorg. Med. Chem, vol. 15, pp. 1181-1205, 2007.
Y. Tsukimi, et al.: "Recent Advances in Gastrointestinal Pathophysiology: Role of Heat Shock Proteins in Mucosal Defense and Ulcer Healing," Biol. Pharm. Bull., vol. 24, No. 1, pp. 1-9, Jan. 2001.
S. Okabe, et al.: "An Overview of Acetic Acid Ulcer Models: The History and State of the Art of Peptic Ulcer Research," Biol. Pharm. Bull., vol. 28, No. 8, pp. 1321-1341, Aug. 2005.
K. Tokuhara, et al.: "Rebamipide, anti-gastric ulcer drug, up-regulates the induction of iNOS in proinflammatory cytokine-stimulated hepatocytes," Nitric Oxide, vol. 18, pp. 28-36, 2008.
R. Utley: "Effect of cimetidine and omeprazole on aspirin- and taurocholate-induced gastric mucosal damage in the rat," Gut, vol. 26, pp. 770-775, 1985.
T. Arakawa, et al.: "Rebamipide, Novel Prostaglandin-Inducer, Accelerates Healing and Reduces Relapse of Acetic Acid-Induced Rat Gastric Ulcer: Comparison with Cimetidine," Digestive Diseases and Sciences, vol. 40, No. 11, pp. 2469-2472, Nov. 1995.
K. Murakami, et al.: "Rebamipide Attenuates Indomethacin-Induced Gastric Mucosal Lesion Formation by Inhibiting Activation of Leukocytes in Rats," Digestive Diseases and Sciences, vol. 42, No. 2, pp. 319-325, Feb. 1997.
S. Watanabe, et al.: "Effects of rebamipide on bile acid-induced inhibition of gastric epithelial repair in a rabbit cell culture model," Aliment. Pharmacol. Ther., vol. 10, pp. 927-932, 1996.

* cited by examiner

*Primary Examiner*—Phyllis G. Spivack
(74) *Attorney, Agent, or Firm*—Rothwell, Figg, Ernst & Manbeck, P.C.

(57) ABSTRACT

Provided is a method for treating damage to the gastric mucosa with a cytoprotective agent, comprising administering to a human in need thereof a pharmaceutical composition comprising an effective amount for treating damage to gastric mucosa of a pharmaceutically acceptable salt of revaprazan as the cytoprotective agent, and a pharmaceutically acceptable carrier. Revaprazan or its salt has an excellent treatment effect for gastrointestinal mucosal damage by potentiating a defensive factor in the gastrointestinal mucosa, simultaneously with acting as an acid pump antagonist.

21 Claims, 5 Drawing Sheets

40mg/kg Indomethacin

10mg/kg Revaprazan + 40mg/kg Indomethacin

EtOH

10mg/kg Revaprazan + EtOH

METHOD FOR TREATING DAMAGE TO GASTRIC MUCOSA

CROSS-REFERENCE TO RELATED PATENT APPLICATION

This application claims priority from Korean Patent Application No. 10-2005-0116567, filed on Dec. 1, 2005, in the Korean Intellectual Property Office, the disclosure of which is incorporated herein in its entirety by reference.

FIELD OF THE INVENTION

The present invention relates to a composition for preventing or treating damages of the mucosa in the gastrointestinal tracts, comprising revaprazan or its salt.

DESCRIPTION OF THE RELATED ART

Revaprazan, known by the chemical name, 5,6-dimethyl-2-(4-fluorophenylamino)-4-(1-methyl-1,2,3,4-tetrahydroisoquinolin-2-yl)pyrimidine, is a compound represented by Formula 1 below, and is available as an acid addition salt (e.g., revaprazan hydrochloride) [PCT Publication No. WO96/05177].

<Formula 1>

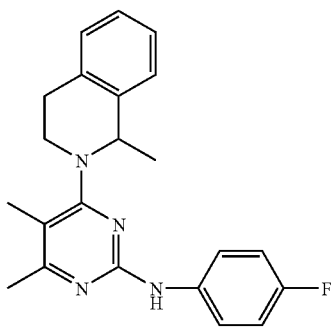

Revaprazan or its salt binds reversibly to a $H^+/K^+$ exchange site of proton pumps ($H^+/K^+$ ATPase) existing in gastric parietal cells to competitively inhibit the secretion of $H^+$ into the gastric lumen. Revaprazan or its salt binds to a specific site of the $H^+/K^+$ ATPase to block the transport of $H^+$ and acid secretion into the gastric lumen, thereby raising intragastric pH. Unlike irreversible proton pump inhibitors such as omeprazole, revaprazan or its salt is not affected by gastric acid activation of the drug or gastric acid secretion of the proton pumps. Based on the mechanism of revaprazan or its salt that is different from that of irreversible proton pump inhibitors such as omeprazole, revaprazan or its salt is classified as an Acid Pump Antagonist (APA).

Meanwhile, gastrointestinal disorders are caused when offensive factors (e.g., gastric acid) are strengthened or defense factors are weakened. Both proton pump inhibitors (e.g., omeprazole) and acid pump antagonists (e.g., revaprazan) are compounds inhibiting the secretion of the offensive factor, i.e., the gastric acid, and cytoprotective agents (e.g., sucralfate, rebamipide) are compounds potentiating defensive factors.

SUMMARY OF THE INVENTION

The present inventors have conducted various clinical trials using an acid pump antagonist, i.e., revaprazan or its salt, and have found that revaprazan or its salt has a cytoprotective activity in the gastrointestinal tracts, beyond proton pump inhibitory activity. Such surprising findings suggest that revaprazan or its salt has not only the effect of inhibiting the secretion of the gastric acid (an offensive factor), but also the gastrointestinal cytoprotective effect of potentiating a defensive factor.

Therefore, the present invention provides a composition for preventing or treating damages of the mucosa in the gastrointestinal tracts, comprising revaprazan or its salt.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
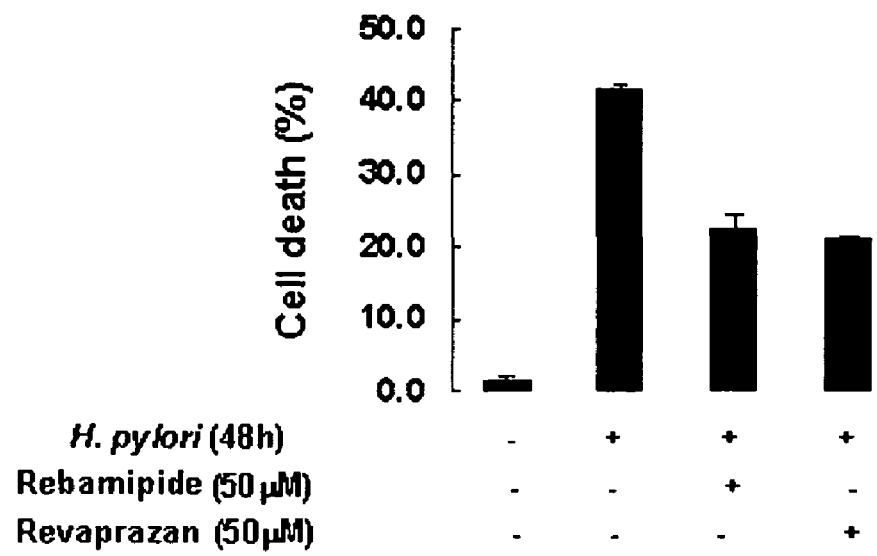
FIG. 1 shows MTT assay results for the inhibitory effect of revaprazan on cell death due to *Helicobacter pylori* (*H. pylori*)-induced gastrointestinal mucosal damage.

The present invention provides a composition for preventing or treating damages of the mucosa in the gastrointestinal tracts, comprising revaprazan or its salt and a pharmaceutically acceptable carrier.

In accordance with one aspect of the present invention, there is provided a method for preventing or treating damage to the gastric mucosa comprising administering to a human in need thereof a pharmaceutical composition comprising an effective amount for preventing or treating damage to gastric mucosa of revaprazan, or a pharmaceutically acceptable salt thereof, and a pharmaceutically acceptable carrier.

In accordance with another aspect of the present invention, there is provided a method for preventing or treating drug-induced damage to the gastric mucosa comprising administering to a human in need thereof a pharmaceutical composition comprising an effective amount for preventing or treating drug-induced damage to gastric mucosa of revaprazan, or a pharmaceutically acceptable salt thereof, and a pharmaceutically acceptable carrier.

In accordance with still another aspect of the present invention, there is provided a method for preventing or treating alcohol-induced damage to the gastric mucosa comprising administering to a human in need thereof a pharmaceutical composition comprising an effective amount for preventing alcohol-induced damage to gastric mucosa of revaprazan, or a pharmaceutically acceptable salt thereof, and a pharmaceutically acceptable carrier.

In accordance with still another aspect of the present invention, there is provided a method for providing cytoprotection of the gastric mucosa in a human receiving non-steroidal anti-inflammatory drugs (NSAIDs), comprising administering to the human prior to or concurrently with NSAIDs a pharmaceutical composition comprising a cytoprotectively effective amount of revaprazan, or a pharmaceutically acceptable salt thereof, and a pharmaceutically acceptable carrier. The NSAIDs used in the present invention are not particularly restricted and include all NSAIDs widely used, such as Aspirin, Indomethacin, Diclofenac, Ibuprofen, Naproxen, Piroxicam, Mefenamic Acid, Flufenamic Acid, Floctafenine, Ethenzamide, Sodium salicylate, Diflunisal, Clofezone, Ketophenylbutazone, Phenylbutazone, Alclofenac, Alminoprofen, Ketoprofen, Flurbiprofen, Pranoprofen, Loxoprofen-Na, Tiaramide hydrochloride, Perisoxal citrate, Emorfazone, Acemetacin, Proglumetacin maleate, Bucolome and the like.

Revaprazan may be prepared according to the methods disclosed in WO96/05177, WO97/42186, and/or WO98/18784. The salt of revaprazan may be an inorganic acid salt such as hydrochloride, sulfate, phosphate, and nitrate, or an organic acid salt such as tartrate, fumarate, citrate, mesylate, and acetate. Revaprazan hydrochloride is preferred.

The composition of the present invention may include additives such as lactose or corn starch, lubricants such as magnesium stearate, emulsifiers, suspending agents, stabilizers, and isotonic agents. If necessary, sweetening agents and/or flavoring agents may be added.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral use, carriers such as lactose, corn starch, and lubricating agents, e.g. magnesium stearate, are commonly added. In the case of capsules for oral administration, lactose and/or dried corn starch can be used as a diluent. When an aqueous suspension is required for oral use, the active ingredient may be combined with emulsifying and/or suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic. The composition of the present invention may be in the form of an aqueous solution containing pharmaceutically acceptable carriers, e.g., saline, at a pH level of 7.4. The solutions may be introduced into a patient's intramuscular blood-stream by local bolus injection.

Revaprazan or its salt can be administered to a patient who needs the prevention or treatment of gastrointestinal mucosal damage in an effective amount ranging from about 50 mg to 400 mg per day, preferably about from 100 mg to 300 mg per day, more preferably about from 150 mg to 250 mg per day, and most preferably about 200 mg per day. Of course, the dosage may be changed according to the patient's age, weight, susceptibility, or symptom.

Hereinafter, the present invention will be described more specifically by the following working examples. However, the following working examples are provided only for illustrations and thus the present invention is not limited to or by them.

EXAMPLE 1

Measurement of Incidence of *Helicobacter pylori* (*H. pylori*)-Induced Cell Death (MTT Assay-1)

In order to determine cytoprotective properties of revaprazan against *H. pylori* infection, gastric mucosal cells were pretreated with revaprazan and rebamipide prior to *H. pylori* infection, and the incidence of cell death was measured. Rebamipide, known to have cytoprotective properties, was used as a control drug.

The human gastric epithelial (AGS, KCLB 21739) cells were seeded onto 96-well plate at $5 \times 10^4$ cells/ml and cultured in RPMI 1640 (Gibco BRL, Grand Island, N.Y., U.S.A.), supplemented with 100 units/mL penicillin, 100 ug/mL streptomycin, and 10% FBS (Fetal Bovine Serum). Revaprazan and rebamipide, dissolved in sterilized water, were added to AGS cells to reach a final concentration of 50 uM and the cells were incubated at 37° C. for 16 hours. To remove RPMI 1640 media, the plate was centrifuged at 24° C., 3000 rpm for 5 minutes and washed three times with PBS (137 mM NaCl, 2.7 mM KCl, 10 mM $Na_2HPO_4$, and 2 mM $KH_2PO_4$). For inoculation, *H. pylori* (ATCC 43504) cultures were resuspended in PBS and cocultured with AGS cells at a final concentration of $5 \times 10^8$ CFU/ml. After 48 hours of incubation at 37° C., the culture was centrifuged at 24° C., 3000 rpm for 5 minutes to remove the culture medium, i.e., RPMI 1640, and then total viable cell numbers were assessed by MTT (3-[4,5-dimethylthiazol-2-yl]-2,5-diphenyl tetrazolim bromide) assay method. 1 mg/ml of an MTT solution prepared by dissolving MTT (Amresco, Ohio, U.S.A.) in PBS (137 mM NaCl, 2.7 mM KCl, 10 mM $Na_2HPO_4$, and 2 mM $KH_2PO_4$) was added to each well (50 μl/well), followed by incubation at 37° C. for 4 hours. The supernatant was then removed by centrifugation at 24° C., 3000 rpm for 5 minutes and the formazan grains formed by the viable cells were dissolved in 99.5% dimethyl sulfoxide (DMSO) (Kanto, Tokyo, Japan) (50 μl/well), and the optical intensity was measured at 540 nm using an ELISA reader (TECAN, Maennedorf, Switzerland).

The MTT assay results are shown in FIG. 1. Referring to FIG. 1, the 48-hour *H. pylori* infection caused significant gastric mucosal cytotoxicity. However, pretreatment of rebamipide and revaprazan was significantly reduced gastric mucosal cytotoxicity by *H. pylori* infection. These results show that revaprazan has cytoprotective effect equal to or greater than rebamipide against *H. pylori*-induced cytotoxicity.

EXAMPLE 2

Measurement of Incidence of Ethanol-Induced Cell Death (MTT Assay-2)

The rat gastric mucosal (RGM-1, RIKEN cell bank, Japan) cells were seeded onto 96-well plate at $5 \times 10^4$ cells/ml and cultured in DMEM-F12 (Gibco BRL, Grand Island, N.Y., U.S.A.), supplemented with 100 units/mL penicillin, 100 ug/mL streptomycin, and 10% FBS (Fetal Bovine Serum). Revaprazan and rebamipide, dissolved in sterilized water, were added to RGM-1 cells to reach a final concentration of 50 uM and the cells were incubated at 37° C. for 16 hours. To remove DMEM-F12 media, the plate was centrifuged at 24° C., 3000 rpm for 5 minutes and washed three times with PBS (137 mM NaCl, 2.7 mM KCl, 10 mM $Na_2HPO_4$, and 2 mM $KH_2PO_4$). Then, ethanol-containing media (200 mM ethanol-containing DMEM-F12, supplemented with 100 units/mL penicillin, 100 ug/mL streptomycin, and 10% FBS) was added to the cells, and the cells were cultured at 37° C. for 16 hours. After the incubation, the culture was centrifuged at 24° C., 3000 rpm for 5 minutes to remove the culture medium and then total viable cell numbers were assessed by MTT (3-[4, 5-dimethylthiazol-2-yl]-2,5-diphenyl tetrazolim bromide) assay method. 1 mg/ml of an MTT solution prepared by dissolving MTT (Amresco, Ohio, U.S.A.) in PBS (137 mM NaCl, 2.7 mM KCl, 10 mM $Na_2HPO_4$, and 2 mM $KH_2PO_4$) was added to each well (50 μl/well), followed by incubation at 37° C. for 4 hours. The supernatant was then removed by centrifugation at 24° C., 3000 rpm for 5 minutes and the formazan grains formed by the viable cells were dissolved in 99.5% dimethylsulfoxide (DMSO) (Kanto, Tokyo, Japan) (50 μl/well), and the optical intensity was measured at 540 nm using an ELISA reader (TECAN, Maennedorf, Switzerland).

Figure 2:
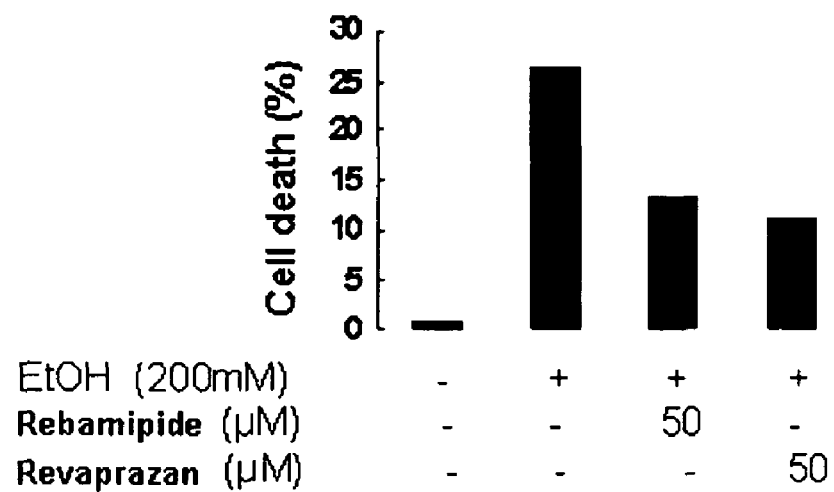
FIG. 2 shows MTT assay results for the inhibitory effect of revaprazan on cell death due to ethanol-induced gastrointestinal mucosal damage.

The MTT assay results are shown in FIG. 2. Referring to FIG. 2, in the ethanol-only treatment group, significant gastric mucosal cytotoxicity was induced. On the other hand, in the rebamipide/revaprazan-ethanol treatment groups, gastric mucosal cytotoxicity was significantly reduced. These results show that revaprazan has cytoprotective effect equal to or greater than rebamipide.

EXAMPLE 3

Evaluation of Preventive Effect of Revaprazan on In Vivo Gastrointestinal Damage Six-week old specific-pathogen-free (SPF) Sprague-Dawley male rats (Charles River, Tokyo, Japan) were used for experiments. The rats were fed a sterilized commercial pellet diet (Biogenomics Co., Seoul, Korea), given sterile water ad libitum, and housed in air-conditioned biohazard room with a 12-h light:12-h dark cycle. The rats were divided into four groups; indomethacin-only treatment group, revaprazan-indomethacin treatment group, ethanol-only treatment group and revaprazan-ethanol treatment group. The rats were food-deprived 24 hours, and then administered with 10 mg/kg revaprazan suspended in 0.5% CMC (carboxymethylcellulose) via oro-gastric tube prior to exposure to either indomethacin (40 mg/kg for 12 hrs) or absolute ethanol (6 ml/kg for 1 hr).

Figure 3A:
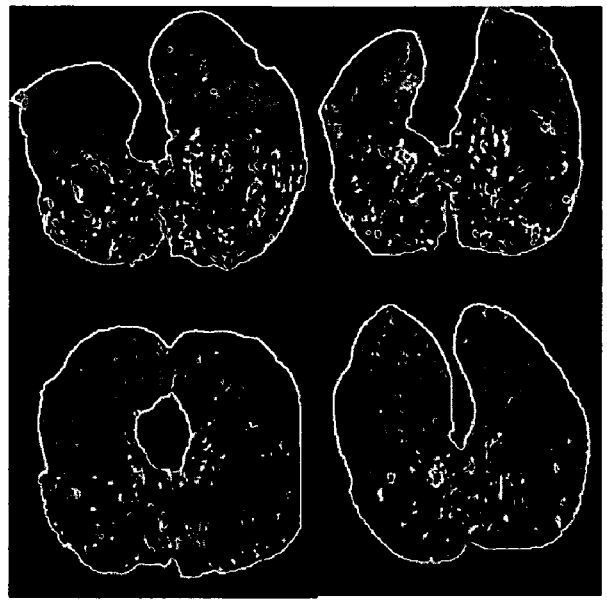
FIGS. 3A and 3B are images showing the cytoprotective effect of revaprazan against in vivo gastrointestinal damage.
Figure 3B:
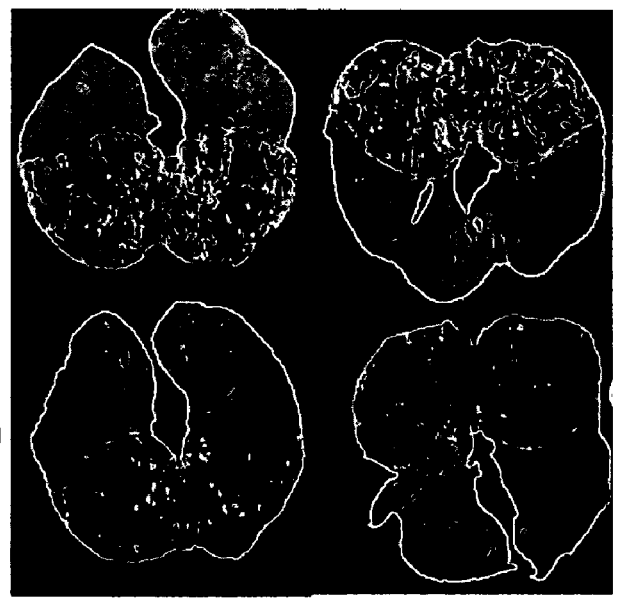

The stomachs of the rats belonging to the groups treated with indomethacin were excised and the degree of gastric mucosal lesions was observed (see FIG. 3A). Referring to FIG. 3A, in the indomethacin-only treatment group, increased hemorrhagic lesions in gastric mucosa were observed visually. However, in the revaprazan-indomethacin treatment group that had been treated with indomethacin after the revaprazan administration, indomethacin-induced gastric injury was completely inhibited. Also, the stomachs of the rats belonging to the ethanol treatment groups were excised and the degree of gastric mucosal lesions was observed (see FIG. 3B). Referring to FIG. 3B, in the ethanol-only treatment group, remarkably increased hemorrhagic lesions in gastric mucosa were also observed visually. However, in the revaprazan-ethanol treatment group that had been treated with ethanol after the revaprazan administration, ethanol-induced gastric injury was completely inhibited. These results show that pretreatment of revaprazan significantly reduced Non-Steroidal Anti-Inflammatory Drug (NSAID) (e.g., indomethacin)- or ethanol-induced gastric mucosal lesions, thereby achieving excellent cytoprotective effect of the gastrointestinal mucosa.

EXAMPLE 4

Evaluation of Activity of Extracellular Signal-Regulated Kinase (ERK) Inducing *H. pylori*-Mediated Cytotoxicity

*H. pylori*-induced cytotoxicity activates MAPK (Mitogen-Activated Protein Kinase), thereby resulting in apoptosis. Therefore, *H. pylori* infection leads to an increase in phosphorylation of ERK among three major subfamilies of MAPKs.

The human gastric epithelial (AGS, KCLB 21739) cells were seeded in culture dishes at $2 \times 10^6$ cells/100 $mm^2$ and cultured in RPMI 1640 (Gibco BRL, Grand Island, N.Y., U.S.A.), supplemented with 100 units/mL penicillin, 100 ug/mL streptomycin, and 10% FBS (Fetal Bovine Serum). Revaprazan, dissolved in sterilized water, were added to AGS cells to reach final concentrations of 5 and 25 uM and the cells were incubated at 37° C. for 16 hours. RPMI 1640 media was removed and then the cells washed three times with PBS (137 mM NaCl, 2.7 mM KCl, 10 mM $Na_2HPO_4$, and 2 mM $KH_2PO_4$). For inoculation, *H. pylori* (ATCC 43504) cultures were resuspended in PBS and cocultured with AGS cells at a final concentration of $5 \times 10^8$ CFU/ml. After 30 minutes of incubation at 37° C., the cells were resuspended in lysis buffer (20 mM Tris-Cl (pH 7.5), 150 mM NaCl, 1% Triton X-100, 1 mM EDTA, and protease inhibitor cocktail (Roche, Mannheim, Germany)). The suspension was sonicated for approximately 10 seconds, four times using the BIORUPTOR (Cosmo Bio, Koto-ku, Tokyo), and centrifuged at 4° C., 12000 rpm for 30 minutes. Supernatants were used as protein extracts, electrophoresed on 10% SDS-PAGE gels, and transferred to PVDF membranes (Millipore, Massachusetts, U.S.A.) using a semidry transfer system (Hoeffer Pharmacia Biotech, San Francisco, Calif., U.S.A.). In order to prevent non-specific binding between the primary antibodies and the proteins, the PVDF membranes were blocked with blocking buffer (TBST: 10 mM Tris-Cl, pH 8.0, 150 mM NaCl, and 0.1% Tween 20 (v/v)) containing 5% skim milk (Difco, Livonia Mich., U.S.A.) for one hour at 23° C. The PVDF membranes were incubated at 4° C. for 15 hours with 1:1000 dilution (200 ng/ml) of primary antibodies for p-ERK or ERK. The PVDF membranes were incubated with 1:2000 dilution (100 ng/ml) of the HRP (horseradish peroxidase)-conjugated secondary antibody (Santa Cruz Biotech, California, U.S.A.) for one hour at 23° C. The immunocomplex was visualized with an ECL (enhanced chemiluminescence) detection kit (Amersham-Pharmacia Biotec, Buckinghamshire, UK).

Figure 4:
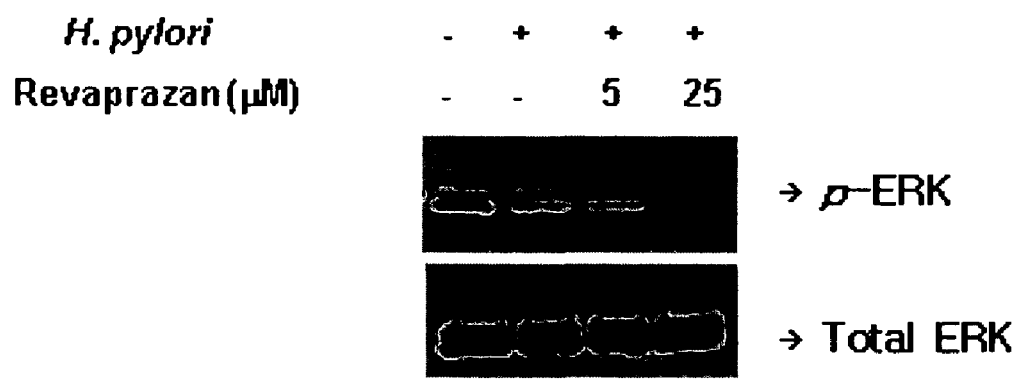
FIG. 4 is a Western blot image showing an inhibitory effect of revaprazan on *H. pylori*-induced ERK (extracellular signal-regulated kinase) activation.

The Western blot results for the p-ERK of the untreatment group and the revaprazan treatment groups of the *H. pylori*-infected cells are shown in FIG. 4. Referring to FIG. 4, revaprazan exhibits a significant, concentration-dependent inhibitory effect on ERK activation.

EXAMPLE 5

Evaluation of Activity of NF-kB Transcription Factor Associated with *H. pylori* Infection (Electrophoretic Mobility Shift Assay, EMSA)

The DNA binding activity of NF-kB (nuclear factor-kappa B), a redox-sensitive transcription factor known to be associated with *H. pylori* infection was evaluated using EMSA. Rebamipide (50 μM), known to have cytoprotective properties, was used as a control drug, and revaprazan (25 μM) was used as a test drug.

The human gastric epithelial (AGS, KCLB 21739) cells were seeded in culture dishes at $2\times10^6$ cells/100 mm$^2$ and cultured in RPMI 1640 (Gibco BRL, Grand Island, N.Y., U.S.A.), supplemented with 100 units/mL penicillin, 100 ug/mL streptomycin, and 10% FBS (Fetal Bovine Serum). Revaprazan and rebamipide, dissolved in sterilized water, were added to AGS cells to reach final concentrations of 25 uM and 50 uM, respectively, and the cells were incubated at 37° C. for 16 hours. The culture media were removed and the cells were twice washed with PBS (137 mM NaCl, 2.7 mM KCl, 10 mM $Na_2HPO_4$, and 2 mM $KH_2PO_4$). For inoculation, *H. pylori* (ATCC 43504) cultures were resuspended in PBS and cocultured with AGS cells at a final concentration of $5\times10^8$ CFU/ml at 37° C. for one hour. The nuclear fractions for EMSA were prepared using the NE-PER Nuclear and the Cytoplasmic Extraction Kit (Pierce, Rockford, Ill., U.S.A.). Sequences of double-stranded oligonucleotides used for EMSA of NF-kB were as follows; 5'-AGT TGA GGG GAC TTT CCC AGG C-3', and the oligonucleotides were labeled with a Biotin 3' End DNA Labeling Kit (Pierce, Rockford, Ill., U.S.A.). The EMSA was performed with a Light Shift Chemiluminescent EMSA Kit (Pierce, Rockford, Ill., U.S.A.).

Figure 5:
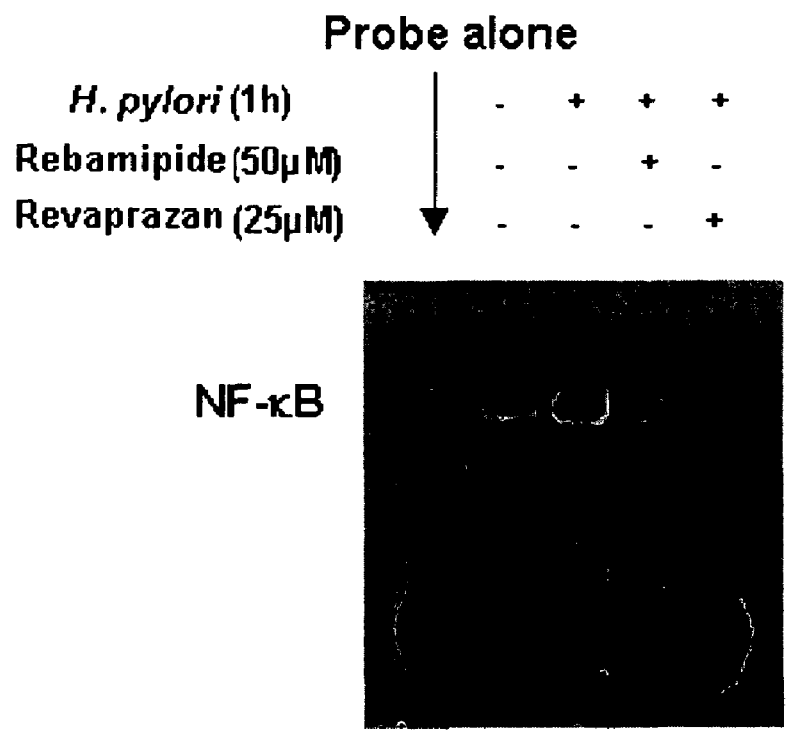
FIG. 5 is Electrophoretic Mobility Shift Assay (EMSA) results showing an inhibitory effect of revaprazan on *H. pylori*-induced NF-kB activation.

The evaluation results for the DNA binding activity of the NF-kB using EMSA are shown in FIG. 5. These results indicated that NF-kB activity was significantly inhibited by revaprazan pretreatment, thereby achieving cytoprotective effect equal to or greater than rebamipide.

EXAMPLE 6

Measurement of Expression Levels of Proteins Participating in Cytoprotection (RT-PCR)

In order to evaluate cytoprotective effect of revaprazan, 100 μM of sulindac belonging to NSAIDs was added to the rat cells, and the expression levels of pro-angiogenic growth factors, VEGF (Vascular Endothelial Growth Factor), interleukin-8 (IL-8), and COX-2 (cyclooxygenase-2) were measured. Rebamipide (50 μM), known to have cytoprotective properties, was used as a control drug and revaprazan (25 μM) was used as a test drug.

The rat gastric mucosal (RGM-1, RIKEN cell bank, Japan) cells were seeded in culture dishes at $2\times10^6$ cells/100 mm$^2$ and cultured in RPMI 1640 (Gibco BRL, Grand Island, N.Y., U.S.A.), supplemented with 100 units/mL penicillin, 100 ug/mL streptomycin, and 10% FBS (Fetal Bovine Serum). Revaprazan and rebamipide, dissolved in sterilized water, were added to RGM-1 cells to reach final concentrations of 25 uM and 50 uM, respectively, and the cells were cultured at 37° C. for 16 hours. The culture media were removed and the cells were washed three times with PBS (137 mM NaCl, 2.7 mM KCl, 10 mM $Na_2HPO_4$, and 2 mM $KH_2PO_4$). A solution of sulindac in DMSO was added to the cells to reach a final concentration of 100 uM and the cells were cultured at 37° C. for 8 hours. The cultured cells were collected by centrifugation at 23° C. at 3000 rpm for 3 minutes, and the total RNA was isolated from the cells using the TRIzol reagent (Life technologies, Milan, Italy). Sterilized RNase-free water was added to 2 μg of the total RNA and 1 μl of 10 pmol/λ oligo dT to obtain reaction solutions with a volume of 34 μl. The reaction solutions were incubated at 65° C. for 5 minutes, and 10 μl of a 5× reverse-transcription buffer, 5 μl of 10 mM dNTPs, and 1 μl of M-MLV reverse transcriptase were added thereto. The resultant solutions were incubated at 37° C. for one hour to obtain cDNA (Promega, Madison, Wis.), and the cDNA were amplified by PCR. The PCR was performed using the Premix Ex Taq kit (Takara, Chiba, Japan) with specific primers as follows; 5'-TGCACCCACGACA-GAAGGGGA-3' and 5'-TCACCGCCTTGGCTTGTCA-CAT-3' (for VEGF); 5'-GAAGATAGATTGCCCGA-3' and 5'-CATAGCCTCTCACACATTTC-3' (for 1 L-8); 5'-ATCT-GTGTGGGTACAAATTTG-3' and 5'-GTCTCTCATCTG-CAATAATGTG-3' (for COX-2); 5'-TGAAGGTCGGTGT-CAACGGATTTGTC-3' and 5'-CATGTAGGCCATGAGGTCCACCAC-3' (for GAPDH). As described above, GAPDH was used as positive control. The PCR was performed as follows: 35 cycles (VEGF, IL-8, and COX-2) or 28 cycles (GAPDE) of 94° C. for one minute, 60° C. (VEGF), 45° C. (IL-8), 48° C. (COX-2), and 55° C. (GAPDH) for one minute (each), and 72° C. for one minute. The PCR product was resolved on 1% agarose gels, and stained with 10 mg/ml of an ethidium bromide.

Figure 6:
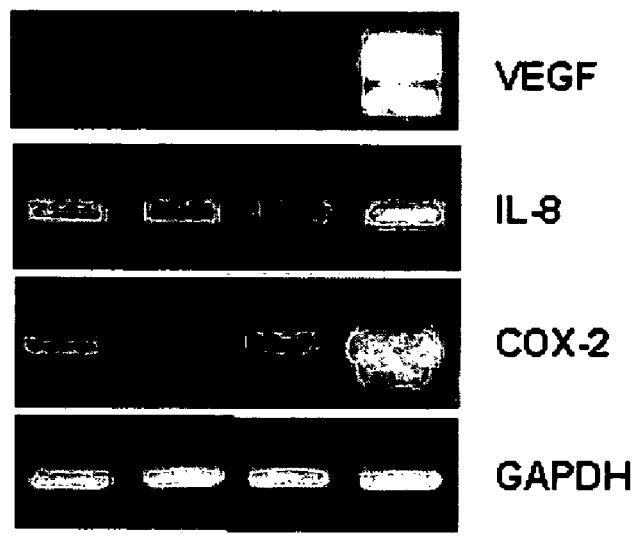
FIG. 6 is RT-PCR results showing an effect of revaprazan on the activity of pro-angiogenic growth factors.

The expression levels of IL-8, VEGF, and COX-2 in the rebamipide-sulindac treatment group and the revaprazan-sulindac treatment group are shown in FIG. 6. Referring to FIG. 6, the expression levels of IL-8, VEGF, and COX-2 in the revaprazan-sulindac treatment group were much higher than those in the rebamipide-sulindac treatment group. It is known that one of mechanisms contributing to NSAID-induced gastric mucosal damage is associated with a reduction in VEGF, IL-8, and COX-2 causing gastric mucosal regeneration and ischemia. In this regard, the results of FIG. 6 showing the increased expression levels of IL-8, VEGF, and COX-2 in the revaprazan-sulindac treatment group reveal that revaprazan has a good cytoprotective effect for the gastrointestinal mucosa.

EXAMPLE 7

Evaluation of Activities of Heat-Hock Proteins (Western Blotting)

To measure expression of heat-shock proteins, HO-1, HSP27, HSP70, cells were pretreated with concentrations of 5, 10, and 25 μM revaprazan, and then treated with indomethacin (a NSAID, 0.5 μM).

The rat gastric mucosal (RGM-1, RIKEN cell bank, Japan) cells were seeded in culture dishes at $2\times10^6$ cells/100 mm$^2$ and cultured in DMEM-F12 (Gibco BRL, Grand Island, N.Y., U.S.A.), supplemented with 100 units/mL penicillin, 100 ug/mL streptomycin, and 10% FBS (Fetal Bovine Serum). RGM-1 cells were pretreated with revaprazan (5, 10, and 25 uM) and cultured 37° C. for 16 hours. The culture media were removed and the cells were washed three times with PBS (137 mM NaCl, 2.7 mM KCl, 10 mM $Na_2HPO_4$, and 2 mM $KH_2PO_4$). A solution of indomethacin in sterilized water was added to the cells to reach a final concentration of 0.5 uM, and the cells were incubated at 37° C. for 16 hours. After incubation, the cells were resuspended in a lysis buffer (20 mM Tris-Cl (pH 7.5), 150 mM NaCl, 1% Triton X-100, 1 mM EDTA, and protease inhibitor cocktail (Roche, Mannheim, Germany)). The suspension was sonicated for approximately 10 seconds, four times using the BIORUPTOR (Cosmo Bio, Koto-ku, Tokyo), and centrifuged at 4° C., 12000 rpm for 30 minutes. Supernatants were used as protein extracts, the extracted proteins were electrophoresed on 10% SDS-PAGE gels and transferred to PVDF membranes (Millipore, Mass., U.S.A.) using a semidry transfer system (Hoeffer Pharmacia Biotech, San Francisco, Calif., U.S.A.). In order to prevent non-specific binding between the primary antibodies and the proteins, the PVDF membranes were blocked with blocking buffer (TBST: 10 mM Tris-Cl, pH 8.0, 150 mM NaCl, and 0.1% Tween 20 (v/v)) containing 5% skim milk (Difco, Livonia Mich., U.S.A.) for one hour at 23° C. The PVDF membranes were incubated at 4° C. for 15 hours with 1:1000 dilution (200 ng/ml) of the primary antibodies for HO-1, HSP27, HSP70 or α-tubulin (TU-02). The PVDF membranes were incubated with 1:2000 dilution (100 ng/ml) of HRP (horseradish peroxidase)-conjugated secondary antibody (Santa Cruz Biotech, California, U.S.A.) for one hour at 23° C. The immunocomplex was visualized with an ECL (enhanced chemiluminescence) detection kit (Amersham-Pharmacia Biotec, Buckinghamshire, UK) (see FIG. 7).

Figure 7:
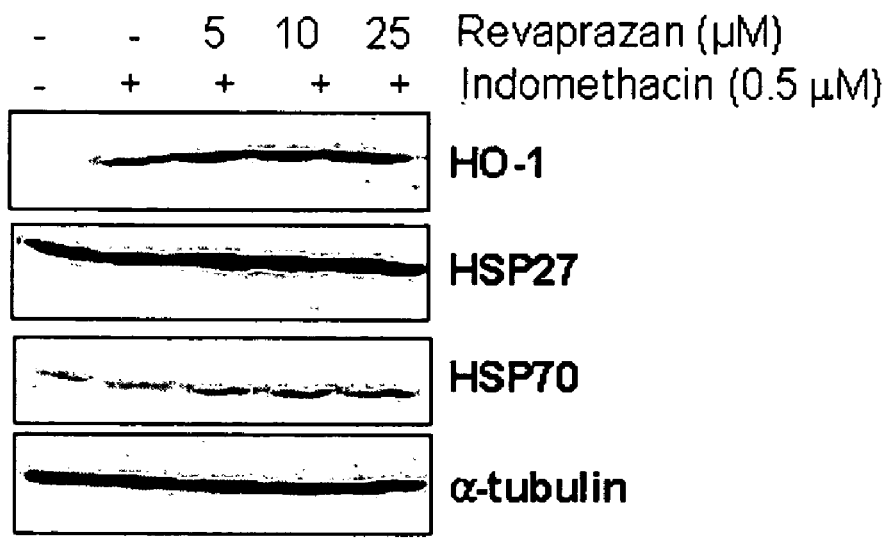
FIG. 7 is a Western blot image showing an effect of revaprazan on the activity of heat-shock proteins.

It can be seen from FIG. 7 that revaprazan exhibits the cytoprotective effect by stimulating expression of heat-shock proteins.

EXAMPLE 8

Evaluation of the Preventive Effect of Revaprazan on NSAID-Induced Gastropathy Six-week old specific-pathogen-free (SPF) Sprague Dawley male rats (Charles River, Tokyo, Japan) were used for experiments. The rats were fed a sterilized commercial pellet diet (Biogenomics Co., Seoul, Korea), given sterile water ad libitum, and housed in air-conditioned biohazard room with a 12-h light:12-h dark cycle. The rats were food-deprived 24 hours, and then administered with 5, 10 mg/kg revaprazan, 30 mg/kg rebamipide and 5 mg/kg omeprazole suspended in 0.5% CMC (carboxymethylcellulose) via oro-gastric tube prior to exposure to indomethacin (40 mg/kg for 12 hrs). Phosphate-buffered saline was perfused into the gastric lumen of the rats to swell the stomachs. Then, the stomachs were opened by an incision along the greater curvature, and the total area of the gastric mucosal lesions was calculated to obtain the average size of the lesions.

Figure 8:
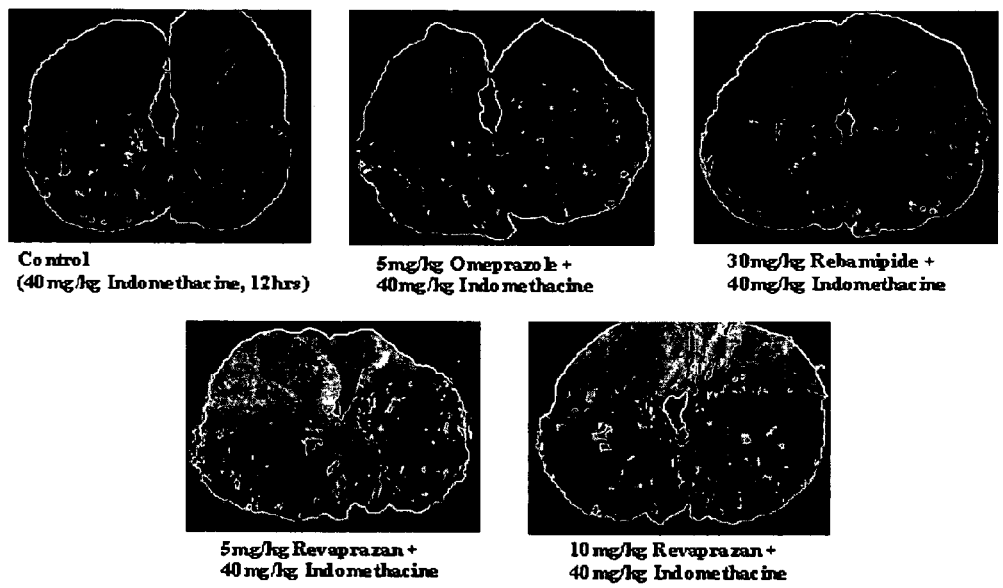
FIG. 8 is a comparative image showing the preventive effects for gastric mucosal lesions with the treatment of rebamipide, omeprazole, and revaprazan prior to indomethacin administration.

Comparative results of the preventive effects for gastric mucosal lesions in the control group and the test groups are shown in FIG. 8. Referring to FIG. 8, hemorrhagic lesions are observed in the control group, the omeprazole pretreatment group, and the rebamipide pretreatment group, whereas little hemorrhagic lesions are observed in the revaprazan pretreatment group. These results show that revaprazan has an excellent preventive effect on gastric mucosal lesions.

EXAMPLE 9

Evaluation of the Treatment Effect of Revaprazan on NSAID-Induced Gastropathy Six-week old specific-pathogen-free (SPF) Sprague Dawley male rats (Charles River, Tokyo, Japan) were used for experiments. The rats were fed a sterilized commercial pellet diet (Biogenomics Co., Seoul, Korea), given sterile water ad libitum, and housed in air-conditioned biohazard room with a 12-h light:12-h dark cycle. The rats were food-deprived 24 hours, and then treated with 1 ml of a solution of indomethacin (40 mg/kg) in 0.5% CMC (carboxymethylcellulose) via oro-gastric tube. 8 hours after the indomethacin treatment, the rats were treated with 1 ml of a solution of revaprazan (5 mg/kg and 10 mg/kg) in 0.5% CMC for one hour, and the degree of gastropathy was determined in the same manner as in Example 8.

Figure 9:
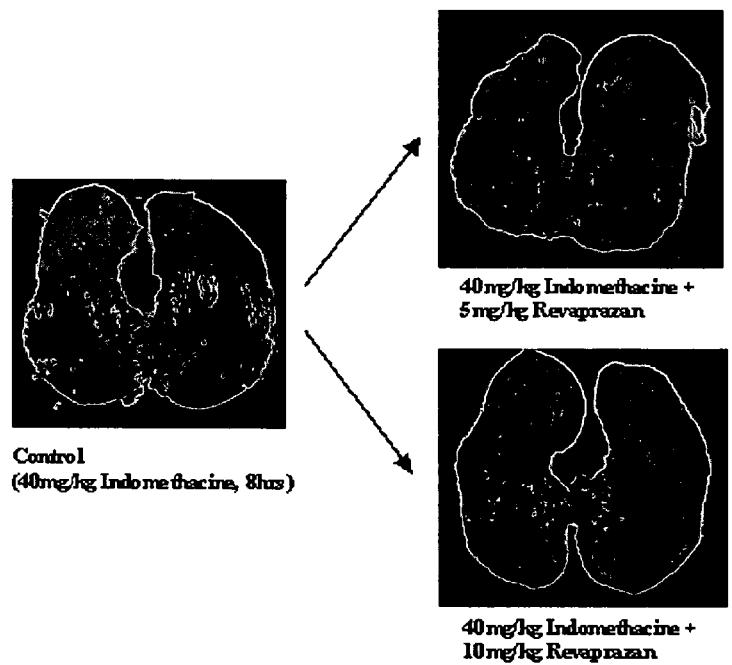
FIG. 9 is a comparative image showing the treatment effect of revaprazan for gastric mucosal lesions after indomethacin administration.

Comparative results of the treatment effects for gastric mucosal lesions in the indomethacin-only treatment group and the indomethacin-revaprazan treatment groups are shown in FIG. 9. Referring to FIG. 9, in the indomethacin-revaprazan treatment groups, gastric mucosal hemorrhagic lesions were remarkably improved and the number of erosions and ulcers was also reduced. These results show that revaprazan has an excellent treatment effect for gastric mucosal lesions.

As described above, revaprazan or its salt has an excellent preventive or treatment effect for gastrointestinal mucosal damage by potentiating a defensive factor in the gastrointestinal mucosa, simultaneously with acting as an acid pump antagonist.

What is claimed is:

1. A method for providing cytoprotection to the gastric mucosa, comprising administering to a human in need thereof a pharmaceutical composition comprising an effective amount for providing cytoprotection to the gastric mucosa of a pharmaceutically acceptable salt of revaprazan and a pharmaceutically acceptable carrier.

2. The method of claim 1, wherein the gastric mucosa has drug-induced damage.

3. The method according to claim 2, wherein the pharmaceutically acceptable salt is revaprazan hydrochloride.

4. The method according to claim 2, wherein the effective amount is about 100 mg to 300 mg per day.

5. The method according to claim 2, wherein the effective amount is about 150 mg to 250 mg per day.

6. The method according to claim 2, wherein the effective amount is about 200 mg per day.

7. The method of claim 1, wherein the gastric mucosa has alcohol-induced damage.

8. The method according to claim 7, wherein the pharmaceutically acceptable salt is revaprazan hydrochloride.

9. The method according to claim 7, wherein the effective amount is about 100 mg to 300 mg per day.

10. The method according to claim 7, wherein the effective amount is about 150 mg to 250 mg per day.

11. The method according to claim 7, wherein the effective amount is about 200 mg per day.

12. The method according to claim 1, wherein the pharmaceutically acceptable salt is revaprazan hydrochloride.

13. The method according to claim 1, wherein the effective amount is about 100 mg to 300 mg per day.

14. The method according to claim 1, wherein the effective amount is about 150 mg to 250 mg per day.

15. The method according to claim 1, wherein the effective amount is about 200 mg per day.

16. The method according to claim 1, wherein the gastric mucosa has the damage caused by cell death due to an infection of *Helicobacter pylori*.

17. A method for providing cytoprotection to the gastric mucosa in a human receiving non-steroidal anti-inflammatory drugs (NSAIDs), comprising administering to the human prior to or concurrently with NSAIDs a pharmaceutical composition comprising a cytoprotectively effective amount of a pharmaceutically acceptable salt of revaprazan and a pharmaceutically acceptable carrier, wherein revaprazan provides the cytoprotection.

18. The method according to claim 17, wherein the pharmaceutically acceptable salt is revaprazan hydrochloride.

19. The method according to claim 17, wherein the effective amount is about 100 mg to 300 mg per day.

20. The method according to claim 17, wherein the effective amount is about 150 mg to 250 mg per day.

21. The method according to claim 17, wherein the effective amount is about 200 mg per day.

* * * * *